(12) United States Patent
Sharim

(10) Patent No.: US 7,833,247 B2
(45) Date of Patent: Nov. 16, 2010

(54) ORTHOPEDIC CLAMPS

(75) Inventor: Hamid Sharim, Kochav Yair (IL)

(73) Assignee: Facet-Med Ltd., Herzeliya Pituach (IL)

( * ) Notice: Subject to any disclaimer, the term of this patent is extended or adjusted under 35 U.S.C. 154(b) by 526 days.

(21) Appl. No.: 10/560,901

(22) PCT Filed: Jun. 17, 2004

(86) PCT No.: PCT/IL2004/000524

§ 371 (c)(1),
(2), (4) Date: Dec. 16, 2005

(87) PCT Pub. No.: WO2004/110288

PCT Pub. Date: Dec. 23, 2004

(65) Prior Publication Data

US 2006/0293658 A1    Dec. 28, 2006

Related U.S. Application Data

(60) Provisional application No. 60/478,855, filed on Jun. 17, 2003.

(51) Int. Cl.
*A61B 17/80* (2006.01)
(52) U.S. Cl. .................................................. 606/248
(58) Field of Classification Search ............... 606/61, 606/69, 70, 71, 86 R
See application file for complete search history.

(56) References Cited

U.S. PATENT DOCUMENTS

| | | | |
|---|---|---|---|
| 4,913,134 A | 4/1990 | Luque | |
| 5,133,717 A * | 7/1992 | Chopin | 606/301 |
| 5,267,999 A | 12/1993 | Olerud | |
| 5,306,275 A * | 4/1994 | Bryan | 606/61 |
| 5,387,212 A | 2/1995 | Yuan et al. | |
| 5,582,612 A | 12/1996 | Lin | |
| 5,665,086 A * | 9/1997 | Itoman et al. | 606/64 |
| 6,235,033 B1 * | 5/2001 | Brace et al. | 606/69 |
| 6,458,131 B1 | 10/2002 | Ray | |
| 2003/0135210 A1 * | 7/2003 | Dixon et al. | 606/61 |

FOREIGN PATENT DOCUMENTS

EP    1121903 A2 *    8/2001

OTHER PUBLICATIONS

Gaines, Jr., R.W., "The Use of Pedicle-Screw Internal Fixation for the Operative Treatment of Spinal Disorders", *The Journal of Bone and Joint Surgery*, pp. 1458-1476, (2000).

* cited by examiner

*Primary Examiner*—Eduardo C Robert
*Assistant Examiner*—David Comstock

(57) ABSTRACT

A saddle clamp for mounting on a bone with curved surface in a bone-fixing or spinal fusion operation, for carrying a bone-fixing member. The saddle clamp has a rigid body with at least two holes for passing fixing elements to be tightened to the bone and at least one assembly element integral with the body for attaching the bone-fixing member. The rigid body has a contact surface configured to allow at least three points of contact with the curved surface of the bone when the saddle clamp is mounted thereon, at least two of the holes passing through the contact surface at least adjacent to two of the points of contact so as to provide, upon tightening of the fixing elements, at least three spaced apart, non-collinear areas of contact and thereby firm attachment of the saddle clamp to the bone.

15 Claims, 6 Drawing Sheets

ORTHOPEDIC CLAMPS

CROSS-REFERENCE

This is a National Phase Application filed under 35 U.S.C. §371 as a national stage of PCT/IL2004/000524, filed on Jun. 17, 2004, claiming the benefit under 35 U.S.C. §119(e) of U.S. Provisional Application No. 60/478,855, filed on Jun. 17, 2003, the content of each of which is hereby incorporated by reference in its entirety.

FIELD OF THE INVENTION

The present invention relates to the field of the orthopedic surgery, in particular as performed by use of mechanical clamps for fixation of neighboring vertebrae or fractured tubular bones.

BACKGROUND OF THE INVENTION

Vertebral fusion is a common spinal surgical procedure, performed in order to overcome problems related to impaired mutual interaction between neighboring vertebrae. A pair of adjacent human vertebrae is shown in FIG. 1. Each of the vertebrae 10 and 20 has, respectively, a vertebra body 11 (21), two pedicles 12 (22), two transverse processes 13 (23), two laminae 14 (24), a spinal process 15 (25), two superior facets 16 (26), and two inferior facets 17 (27). The body of the pedicle 12 is attached by its base end to the vertebra body 11, while its top end branches into the transverse process 13, the superior facet 16 and the lamina 14. The inferior facet 17 is attached to the lamina 14. The two laminae 14 are connected to either side of the spinal process 15 and, together with the pedicles 12 and the vertebra body 11, form a channel 18 sheltering the spinal cord. The superior facets 26 of the lower vertebra 20 and the inferior facets 17 of the upper vertebra 10 form two facet joints 19. A spinal disc 29 connects elastically each two adjacent vertebrae. (The same numerals will be used throughout to designate same parts of the vertebra.)

There are a number of indications requiring spinal fusion operations including:

(i) traumatic fracture of the vertebral body;

(ii) degenerative disc or vertebral disease, such as disc herniation, instability of the facet joint, compressive radiculopathy;

(iii) following the failure of previous spinal surgery, or the removal of a disc;

(iv) chronic vertebral or disc infection;

(v) vertebral instability, such as in spondylolisis or spondylolystetis; and (vi) following the removal of spinal tumors.

The technique involves the disablement of the relative motion between adjacent vertebrae to prevent compression during body movements and for stabilizing the spinal column. Spinal fusion is a very common procedure, with over 400,000 such procedures performed annually in the USA alone.

Three methods are currently generally used for performing this procedure;

(a) Fixation of the rear of the vertebrae by means of hooks, two of which are generally used to hook onto the laminae on either side of the vertebrae, and connection between them by means of a metallic rod, as exemplified by U.S. Pat. No. 5,267,999. The method is illustrated schematically in FIG. 2 where a clamp 30 is fixed by hooks 32 and 34 to the lamina 14 of the vertebra 10.

(b) Pedicle screw insertion into the body of the vertebra, for example as described in U.S. Pat. No. 4,913,134. This method involves the insertion of two screws per vertebra, on the left and right spinal pedicles. A rigid rod or an elongated fusion plate is secured under the screw head on either side of the vertebra, thus preventing motion between adjacent vertebra.

The method is illustrated schematically in FIGS. 3A and 3B showing, respectively, cross-sectional and lateral sectional views of vertebral fusion using the pedicle screw procedure. Two pedicle screws 40 with special heads 42 are inserted through the pedicle 12 into the vertebral body 11. Fixing rods 44 are attached under the screw heads 42 to fuse together the vertebrae 10 and 20.

(c) Fixation of the front part of the vertebrae, either by means of screws inserted into the body of the vertebra, or by use of hollow threaded cages inserted into pre-drilled tracts between the vertebrae, and which are filled with bone graft material, which ultimately fuses with the vertebral bodies to consolidate the fusion.

The method is illustrated schematically in FIG. 4 which shows a frontal view of vertebral fusion using the threaded fusion cage procedure. Fusion cages 46 with bone graft material therein 48 are shown inserted between two vertebral bodies 11 and 21, from the front of the spine.

Each of these prior art methods has its own specific disadvantages:

(a) Hook fixation—because of the comparative weakness of the holding power of the hooks, a larger number of vertebrae need to be fused to achieve acceptable results, than when using the other methods. This may lead to unnecessarily limited movement of the spine in the operated region, with consequent problems of mobility. Furthermore, what should be a comparatively simple operation and localized operation becomes much more extensive, with concomitant increase in blood loss, time under anesthesia, and the need for an external brace for some time after the operation. Failure of the hooks to hold well may cause them to move during the healing period.

b) Pedicle screwing—the insertion of the pedicle screw is generally a difficult, error prone and time consuming procedure. The surgeon must determine the entry point and the trajectory of the screw holes from X-ray fluoroscopic images taken from several angles, and this requires expertise and experience, and a well-trained operating room team. Furthermore, the method results in a high level of X-ray exposure to the surgeon and staff. The following problems can arise during this procedure:

(i) Breakage of the pedicle due to a misdirected drill, or poor drilling technique.

(ii) Penetration of the spinal cord, with resultant nerve damage.

(iii) Damage to neighboring nerve roots, causing pain and nerve damage.

(iv) Penetration of the abdominal cavity, with the resultant danger of damage to major blood vessels and hemorrhaging.

(v) Part of the upper tip of the facet joint often needs to be removed to provide room for the pedicle screw head.

A number of clinical studies have reported 10 to 40% misplaced screws, which is defined as a screw more than 2 mm away from the intended ideal position. It has been reported by R. W. Gaines in the article "The Use of Pedicle Screw Internal Fixation for Spinal Disorders", *Journal of Joint and Bone Surgery*, Vol. 82-A, No. 10, 2000, that about 3% of misplaced screws are more than 5 mm away from their planned position, almost inevitably causing nerve damage. Insertion of pedicle screws in the thoracic and cervical vertebrae is even riskier because of the compact and delicate structure of the spine in these regions. For this reason, few experienced surgeons perform spinal fusion by this means at these levels, and in the USA, the procedure is not even FDA authorized for these regions.

(c) Fusion cage—in order to drill the necessary tracts for inserting the cages, or the holes for inserting the screws, this procedure requires one of two major surgical procedures. Either access is needed to the front of the spine through the abdomen or thoracic cavity, with its concomitant possibilities of complications, or access to the vertebrae from the rear, in which case a wide laminectomy procedure must be performed, and displacement of the entire dura matter in the region of the cage insertion Furthermore, in all of the methods, there are the general difficulties relating to surgery on the vertebral column, include micro-movement of the vertebral column during the operation, the inherently small target objects of the procedure such as the pedicles, and delicate nerve tissue close to the operation region.

The disclosures of each of the publications mentioned in this section and in other sections of the specification, are hereby incorporated by reference, each in its entirety.

Fixation of fractured tubular bone fragments is also a common orthopedic surgical procedure. It is performed on long bones of the limbs in order to ensure correct position of the fragments during their natural fusion and better mobility of the patient during healing. An example of internal fixation known in the prior art is shown schematically in FIG. 5. Such fixation of a broken bone 86 usually uses at least three screws 92, at each side of the fracture 94 to fix a supporting plate 96. The operation includes exposure of a rather long area of the bone.

There are also methods for external fixation of fractured bones, all of them involving application of long screws partially remaining above the skin surface to be fixed to the supporting plates. Such screws are likely to cause secondary infections of the operated limb.

SUMMARY OF THE INVENTION

In accordance with the present invention, there is provided a new kind of clamp—"saddle" clamp for mounting on bones with curved surface in a bone fixing or spinal fusion operation, for carrying a bone-fixing member, i.e. plate. The saddle clamp has a rigid body with at least two holes for passing fixing elements to be tightened to the bone and at least one assembly element integral with the body for attaching the bone-fixing member. The rigid body has a contact surface configured to have at least three points of contact with the curved surface of the bone when the saddle clamp is mounted thereon, at least two of the holes passing through the contact surface via or adjacent two of the three points of contact. This allows to provide, upon tightening of the fixing elements, at least three spaced apart, non-collinear areas of contact, and firm attachment of the clamp to the bone.

Preferably, axes of at least two of the holes converge towards the bone.

The assembly element may be a threaded pin protruding from the rigid body or a threaded nut built into the rigid body.

One embodiment of the present invention is a saddle clamp for use in vertebral fusion operation allowing to perform it in a simple, safe and speedy manner, avoiding many of the above-mentioned disadvantages of the prior art methods. The application method of the new saddle clamp provides less likelihood of complications and damage to the patient; especially to the spinal cord or nerves emanating therefrom, or to adjacent blood vessels; it is simple to perform without requiring a high level of surgeon skill, and will not cause catastrophic damage in the event of a poorly executed procedure, it is short and requires minimal X-radiation exposure, and utilizes simple instruments and therefore, does not require a highly skilled operation room team.

The saddle clamp in accordance with this embodiment is designed for mounting on a vertebra having at one side thereof a pedicle, a superior facet with an edge, and a transverse process. The contact surface of the saddle clamp comprises a saddle surface adapted to straddle the top of the pedicle between the transverse process and the superior facet when the clamp is mounted, and a second surface adapted to contact simultaneously the superior facet. One of the passing holes is obtained through the saddle surface, and a second passing hole is obtained through the second surface.

Preferably, the first and the second passing holes are positioned such that, when the clamp is mounted, the axis of the first passing hole is directed into the pedicle and the axis of the second passing hole is directed to the superior facet and is convergent with the axis of the first passing hole.

Preferably, the second surface is an arcuate surface adapted to receive the edge of the superior facet. Preferably, the axis of the second passing hole is then directed into the edge of the superior facet.

Another embodiment of the present invention is a saddle clamp for mounting on a tubular bone, wherein the contact surface is of arcuate shape and axes of at least two holes are directed perpendicular to bone's axis. Preferably, projections of the holes' axes on a cross-section of the tubular bone intersect at an angle between 45° and 60°.

In accordance with a second aspect of the present invention, there is provided a method for mounting the saddle clamp to a bone, the method including:

providing a saddle clamp with suitably configured contact surface and holes for said bone;

providing fixing elements;

exposing a suitable area of the bone;

drilling holes in the bone corresponding to the passing holes, for anchoring the fixing elements; and mounting the saddle clamp on the bone by inserting the fixing elements through the passing holes of the clamp and tightening them in the drilled holes in the bone.

The fixing elements used in the method may be screws, or nails, or expanding anchors. When the fixing elements are screws, the holes in the bone may be pilot holes.

In one embodiment of the method, the bone is tubular and the holes in the bone have axes perpendicular to the axis of the tubular bone. Preferably, projections of the holes' axes on a cross-section of the tubular bone intersect at an angle between 45° and 60°.

In another embodiment of the method, the bone is a vertebra having a vertebra body and, at one side thereof, a pedicle, a superior facet with an edge, and a transverse process, the method including:

providing a saddle clamp where the contact surface of the rigid body comprises a saddle surface adapted to straddle the top of the pedicle between the transverse process and the superior facet, and a second surface adapted to contact simultaneously the superior facet, a first of the passing holes being obtained through the saddle surface and a second of the passing holes being obtained through the second surface;

providing fixing elements;

drilling pilot holes in the vertebra corresponding to the passing holes, for anchoring the fixing elements, without penetrating further than the body of the pedicle, one pilot hole being drilled in the pedicle and a second pilot hole being drilled in the superior facet; and mounting the clamp on the vertebra by inserting the fixing elements through the passing holes of the clamp and tightening them in the drilled pilot holes of the vertebra, without said fixing elements penetrating said vertebra body.

Preferably, the second surface of the clamp is an arcuate surface adapted to receive the edge of the superior facet, and the second pilot hole is drilled into the edge of the superior facet.

The method may include adjusting the surface of the vertebra to the clamp by cutting portion of the superior facet edge.

Preferably, when the fixing elements are screws, a first pilot hole is drilled through the top of the pedicle while a second pilot hole is drilled through the edge of the superior facet with an axis convergent with the axis of the first pilot hole.

The saddle clamps of the present invention needs less invasive surgery (less surgical cuts, less exposed bone tissue, less hemorrhages, etc.). In tubular bone surgery, the clamps are applicable for fixation of long bones with multiple fractures.

In spinal fusion surgery, the method of the present invention allows usage of short and thin screws which penetrate only into the top ends of their respective bone bases. Since the bone structure of the top end of the pedicle is dense (cortical bone), two inclined screws may hold the element firmly and snuggly in its position, despite their short length.

Use of the clamp of the present invention has a number of significant advantages over the prior art methods of performing spinal fusion. Firstly, the short drilling length of the screw holes reduces the likelihood of damage to the spinal cord, or any other adjacent feature, such as nerve ends or blood vessels. Furthermore, the short drilling length, the thinner screw and the drilling into dense cortical bone regions of the pedicle, means that there is little danger of breakage of the pedicle. Additionally, the use of two inclined screws inserted into cortical bone, despite their short length and smaller diameter, provides attachment strength which is as adequate for the required task as that of the prior art use of single pedicle screws on each side. Because of the reduced danger of complications, and the simple physical procedure, the operation can even be performed by less experienced surgeons. Furthermore, the greater simplicity and safety of the use of the clamp of the present invention may make its use more acceptable for application to spinal fusion in the upper parts of the back, which has been hitherto more rarely performed, if at all allowable by the regulatory authorities. Finally, the reduced duration of the operation, typically down to half of that for a similar operation performed using prior art methods, and the reduced radiation exposure, make the use of the clamp of the present invention significantly safer to the patient.

BRIEF DESCRIPTION OF THE DRAWINGS

The present invention will be understood and appreciated more fully from the following detailed description, taken in conjunction with the drawings in which.

DETAILED DESCRIPTION OF THE INVENTION

Figure 6A:
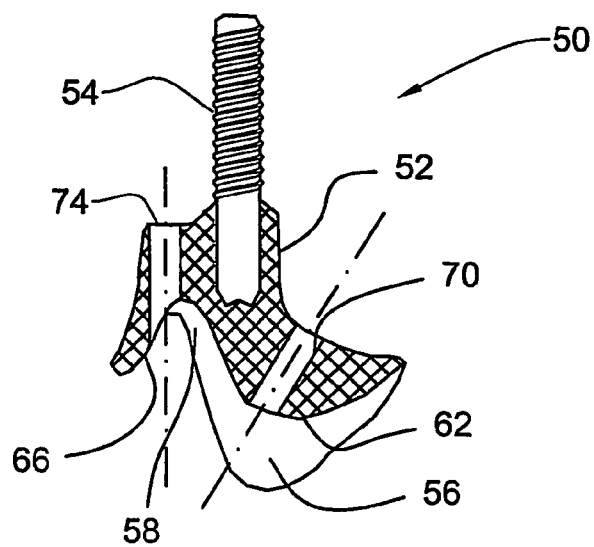
FIGS. 6A to 6E are schematic views of a vertebral fusion saddle clamp according to an embodiment of the present invention, the views being taken from different directions to illustrate the structure of the element.
Figure 6B:
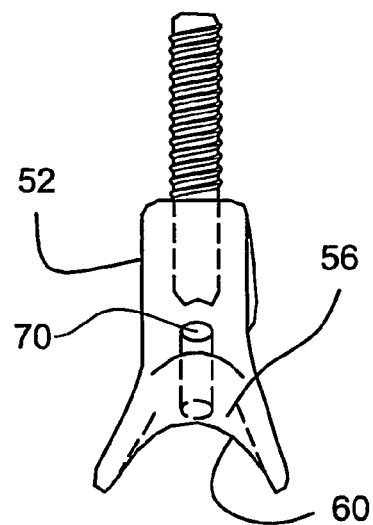
Figure 6C:
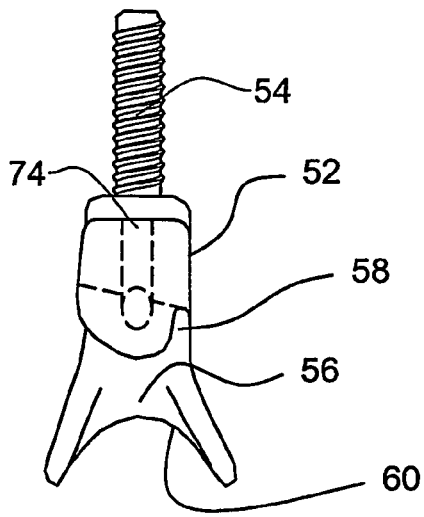
Figure 6D:
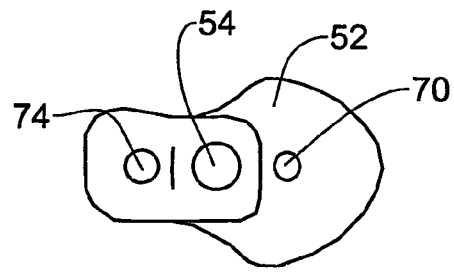
Figure 6E:
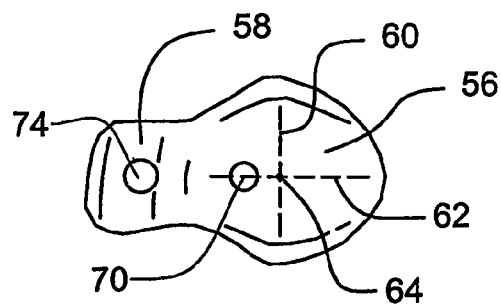

FIGS. 6A to 6E are schematic views of a vertebral fusion clamp 50 according to an embodiment of the present invention, the views being taken from different directions to illustrate the structure of the element. The views are taken respectively from the right side (FIG. 6A), from the rear side (FIG. 6B), from the front side (FIG. 6C), from above (FIG. 6D) and from beneath (FIG. 6E). The vertebral fusion clamp 50 comprises a body 52 and an integral threaded rod 54 for attachment of a fusion plate or rods.

The body 52 has unique shape including a saddle surface 56 and an arcuate surface 58. The saddle surface 56 is defined generally between a down-turned arch 60 and an upturned arch 62 lying in transverse planes and having a common point 64 (saddle point). The arcuate surface 58 is defined generally by a down-turned arch 66 (as seen best in FIG. 6A) and merges smoothly with the saddle surface 56. The top-most points of the arcuate surface 58 are higher than the arch 60.

Figure 7:
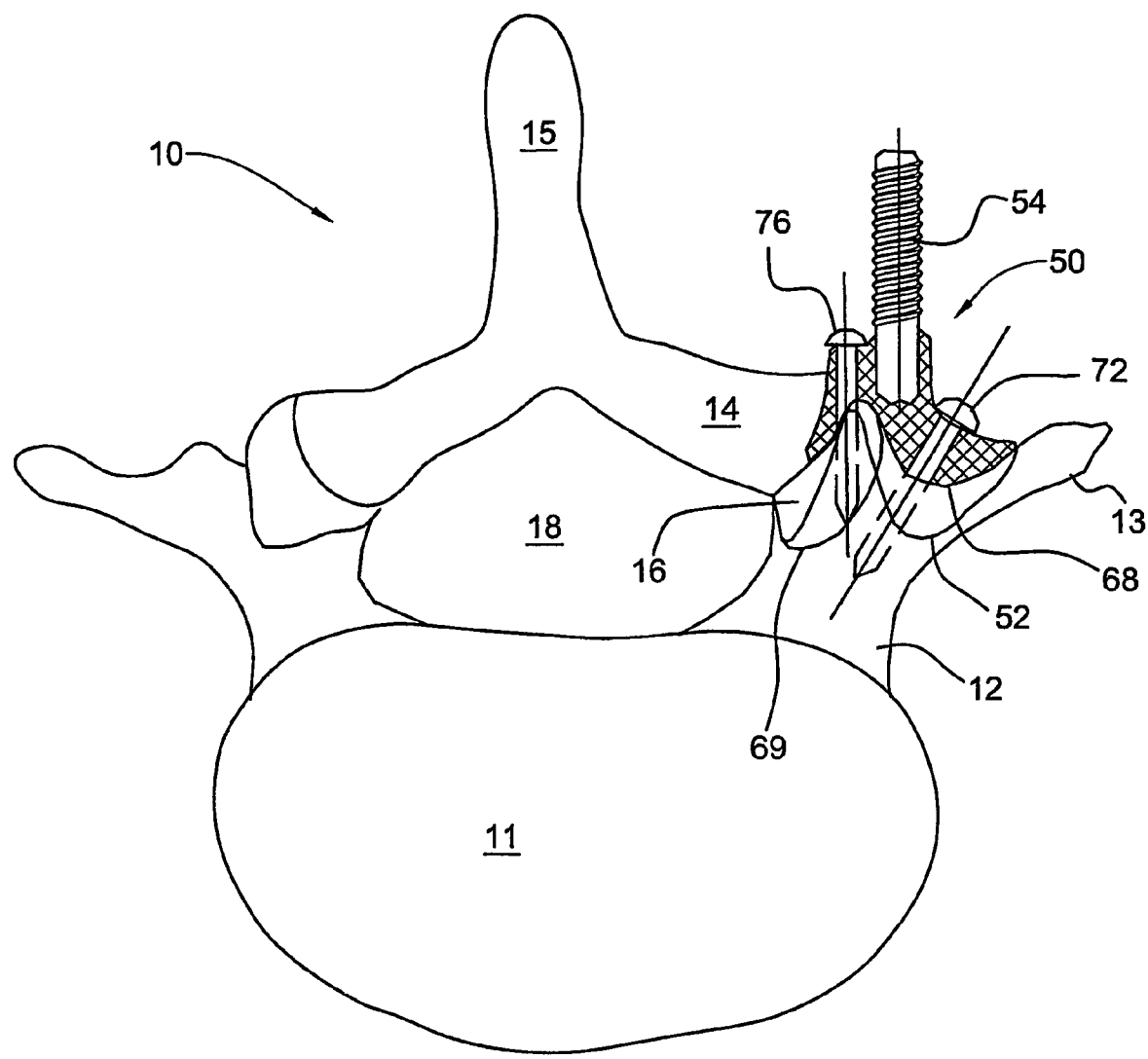
FIG. 7 is a schematic cross-sectional view of a vertebra with the vertebral fusion saddle clamp of the present invention fitted in its predetermined position over the pedicle, the edge of the superior facet and the base of the transverse process.

With reference also to FIG. 7, the saddle surface 56 is shaped to fit the top end 68 of the pedicle 12. It will be appreciated that the top end 68 of the pedicle 12 has roughly saddle shape as well, especially where it branches into the transverse process 13 and the superior facet 16. The corresponding saddle surface 56 allows the clamp 50 to straddle the pedicle top and to sit snuggly thereon in a range of angular positions. When the saddle surface 56 is on the pedicle top, the arcuate surface 58 receives the edge 69 of the superior facet 16 thereby providing for an additional support and better contact between the clamp and the vertebra.

The clamp body 52 has a bore 70 for passing a pedicle fixing screw 72 and a bore 74 for passing a facet fixing screw 76. The bore 70 pierces the saddle surface 56 and is directed into the pedicle top 68, while the bore 74 pierces the arcuate surface 58 and is directed to the facet edge 69. Preferably, the axes of the bores 70 and 74 are directed to converge in the pedicle 12 when the clamp is fitted on the vertebra.

In FIG. 7, the clamp 50 is shown mounted on the vertebra 10 by means of the two fixing screws 72 and 76. Vector sum of the holding force of the two inclined screws is directed down the pedicle, whereby the clamp of the present invention is held firmly on the pedicle, as effectively as in the prior art pedicle screw method. However, as illustrated in FIG. 7, the screws are significantly smaller, they do not penetrate the vertebral body 11, and thus reduce inherent dangers of complications. For example, screws of diameter 2.5-3 mm may be used instead of the conventional 6.5 mm screws.

Figure 1:
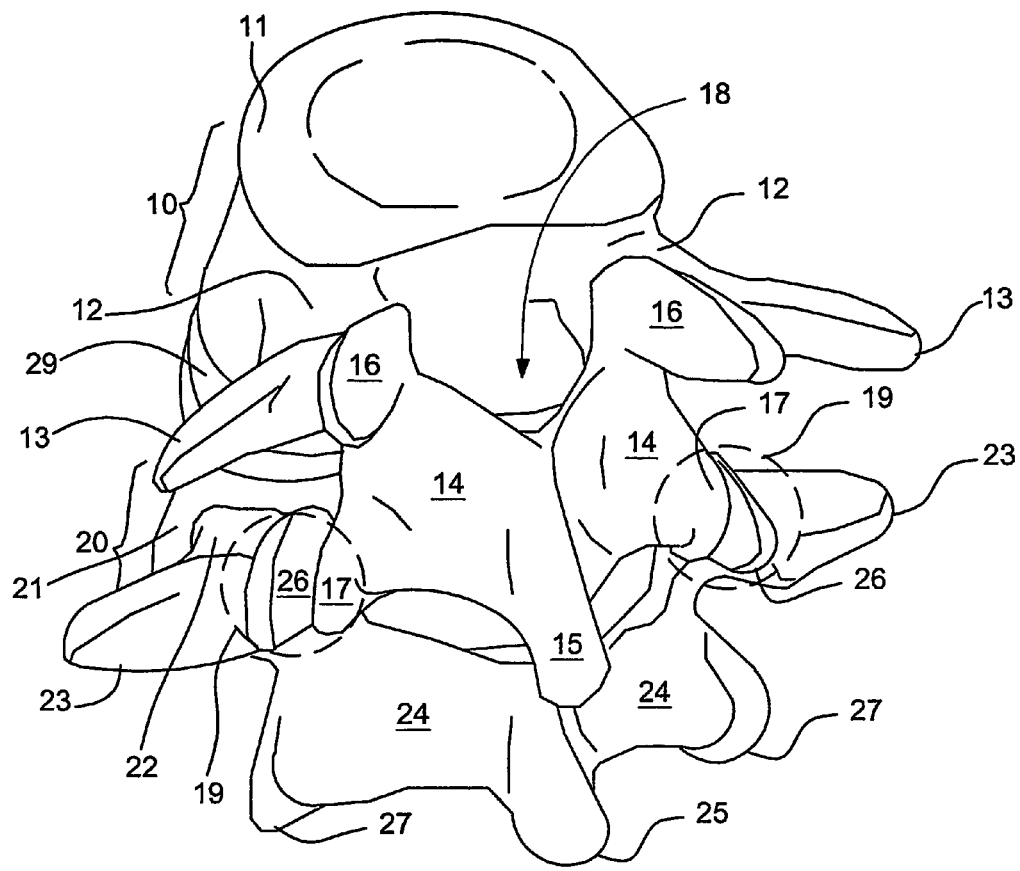
FIG. 1 illustrates the form and the parts of a human vertebra.
Figure 2:
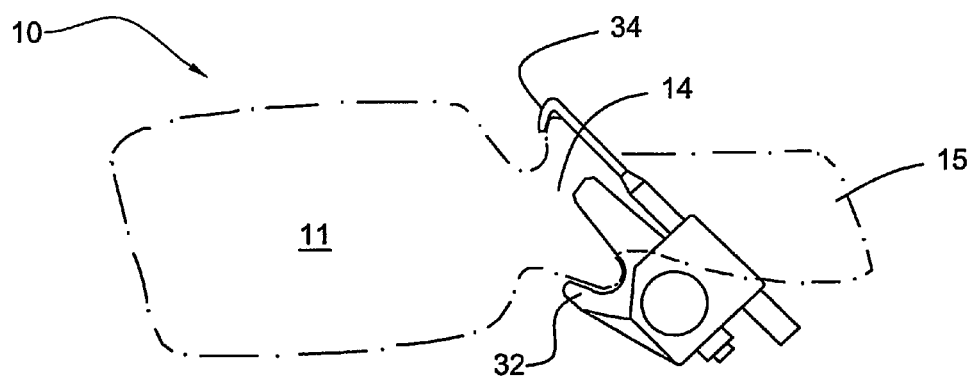
FIG. 2 schematically illustrates a prior art clamp with hook fixation to the laminae of a vertebra.
Figure 3A:
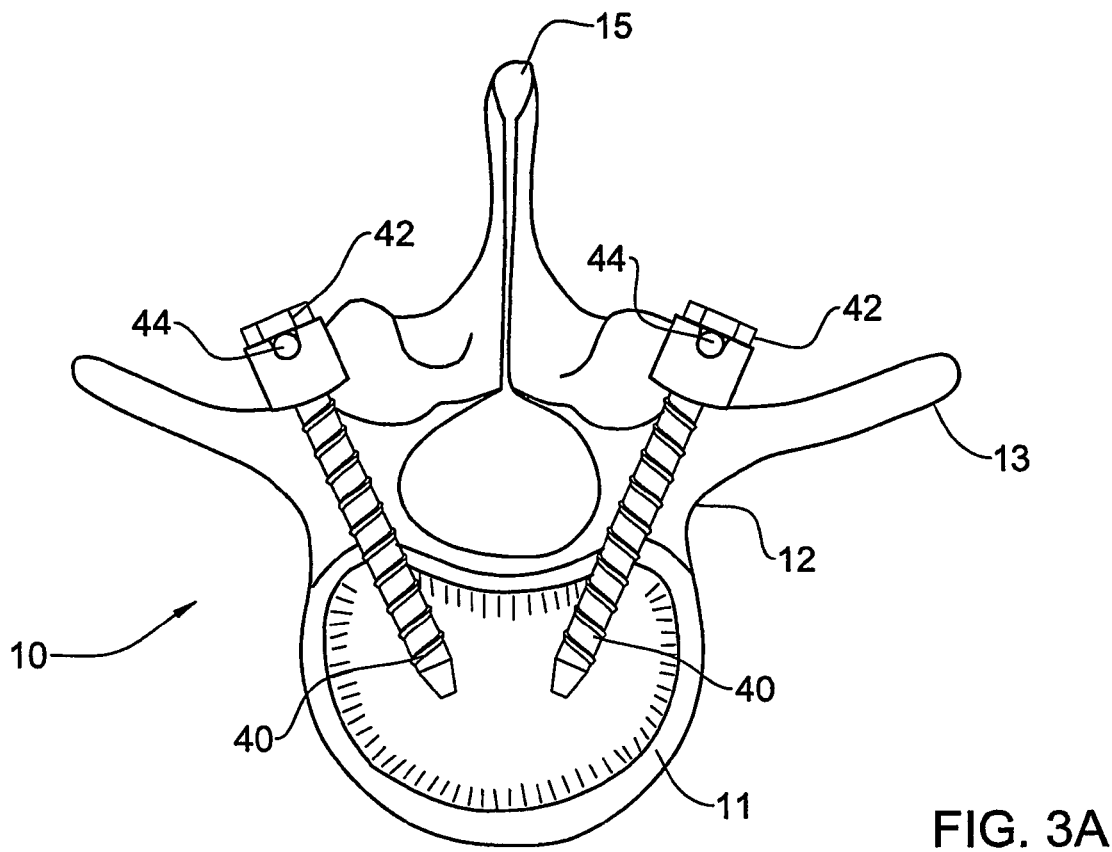
FIGS. 3A and 3B are schematic cross-sectional and lateral views of a prior art vertebral fusion using the pedicle screw procedure.
Figure 3B:
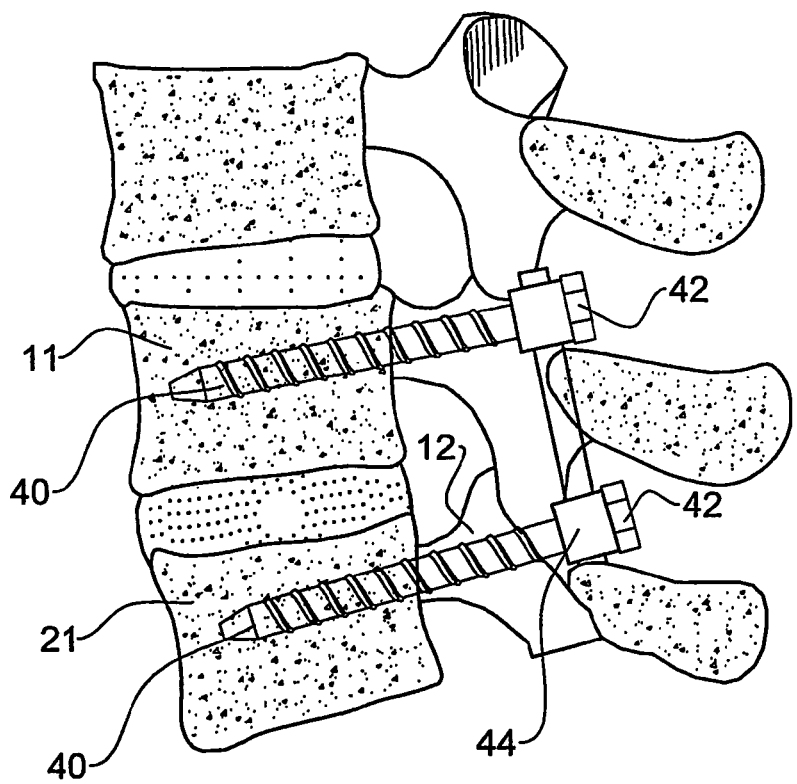
Figure 4:
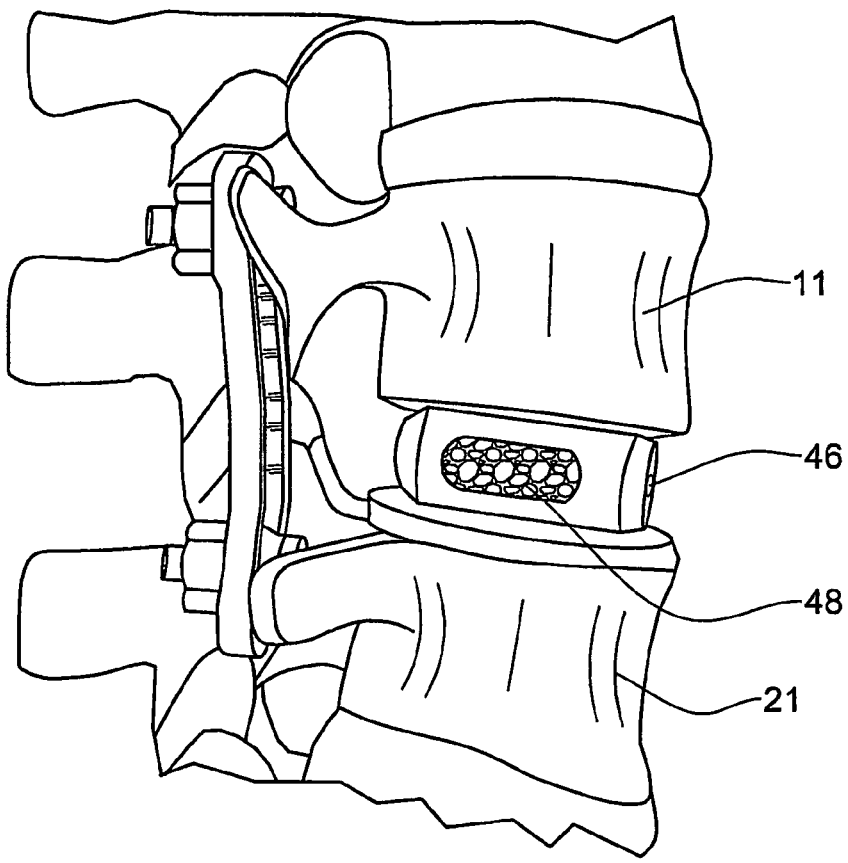
FIG. 4 is a schematic frontal view of a prior art vertebral fusion using the threaded fusion cage procedure.

Though the vertebral fusion clamp of the present invention has been described hereinabove as operating independently, it is to be understood that it can also be used as an additional support device for the cage procedure described in the prior art, to assist in support until the bone grafts 48 within the cage 46 have taken (see FIG. 3).

According to the method of the present invention, an operation routine for performing spinal fusing procedure typically comprises the following steps. The patient is anesthetized, the spinal region where the fusion is to be performed is exposed, and the muscles detached from the various parts of the vertebrae to be treated, as in a normal spinal operation. After preparation of the site on which the vertebral fusion clamp is to sit, the clamp is inserted into position on the pedicle top, and two self-tapping fixing screws are driven into the outer cortical bone of the pedicle and the edge of the superior facet.

Since the fixing screws are of comparatively small diameter, only a very fine pilot hole or an insertion starting position may be drilled. The hole, as the screws themselves, does not go beyond the body of the pedicle and does not penetrate the vertebral body. This feature is one of the important differences between the procedure of the present invention, and the prior art pedicle screw insertion procedure, which generally requires a comparatively large pilot hole to be drilled, with the resulting potential dangers mentioned above.

The surface of the vertebra may be adjusted to the clamp by cutting portions of the superior facet edge.

The above procedure is repeated with all clamps that are needed for the spinal fusing, then the vertebral clamping rods or plates are attached to fuse the chosen vertebrae together, and the patient's back is surgically closed again.

Figure 8:
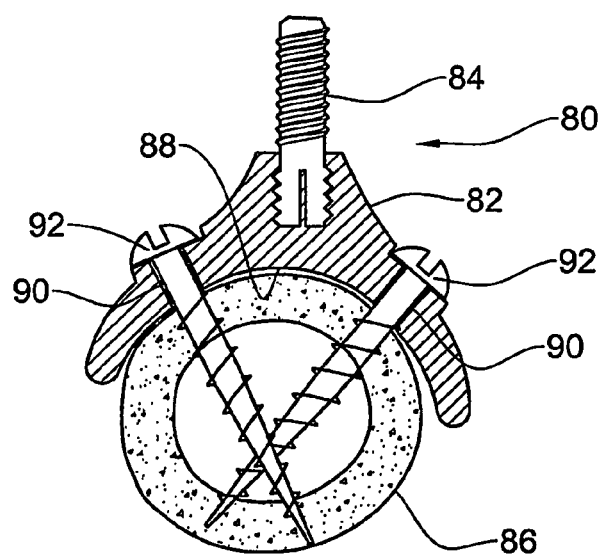
FIG. 8 is a schematic cross-sectional view of a tubular bone with a saddle clamp of the present invention fitted over a solid portion of a fractured bone.

In FIG. 8, there is shown a schematic cross-sectional view of a saddle clamp 80 for use in tubular bones surgery. The saddle clamp 80 comprises an arcuate body 82 and an integral threaded pin 84 anchored in the body. The body 82 includes an arcuate surface 88. The arcuate surface 88 is shaped to fit the generally cylindrical surface 86 of a tubular bone so as to sit snugly for a range of curvatures of the surface 86.

The clamp body 82 has two bores 90 for passing fixing screws 92. The axes of the bores 90 and the fixing screws 92 are perpendicular to the bone axis, at about 45°-60° to each other and converging towards the opposite side of the bone. Preferably, the two bores and the screws are not in one plane.

Figure 9:
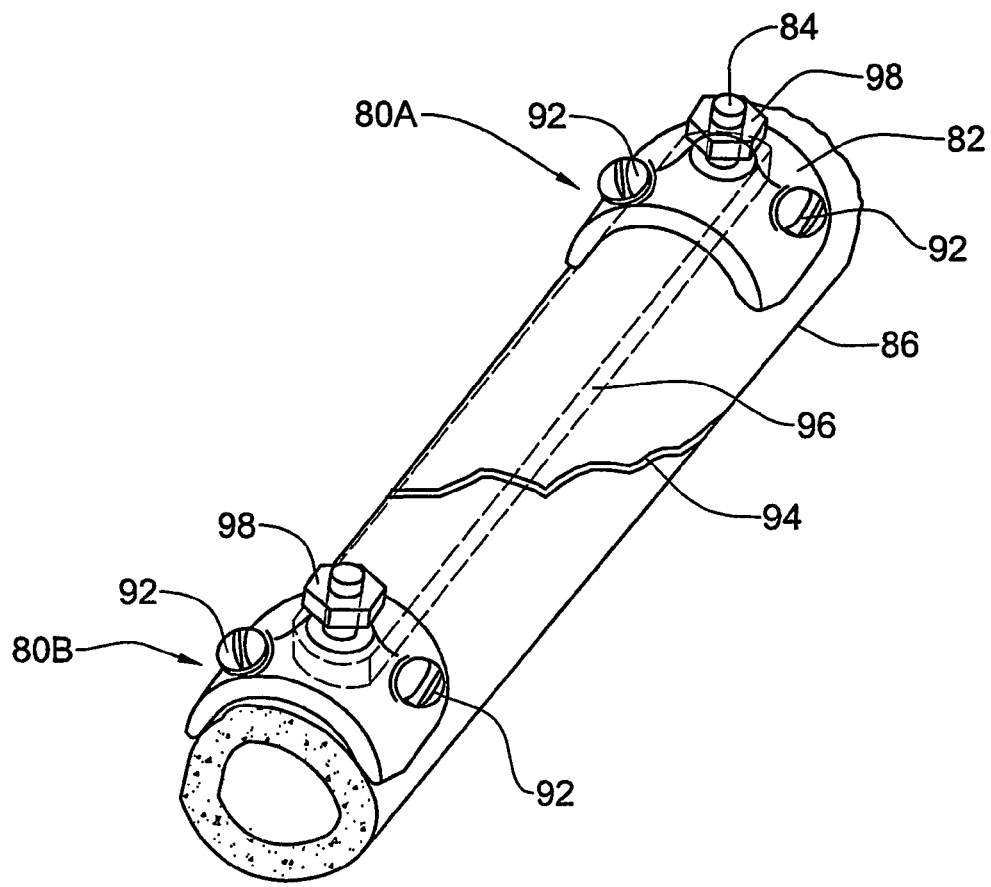
FIG. 9 is a perspective view of a fractured tubular bone fixed by means of one bar and two saddle clamps of the present invention.

FIG. 9 shows two saddle clamps 80A and 80B fitted on non-broken portions of the tubular bone 86 with fracture 94. An elongated plate 96 (shown in broken lines) is tightened by means of nuts 98 on the threaded pins 84 thereby fixing the parts of the fractured bone.

Figure 10:
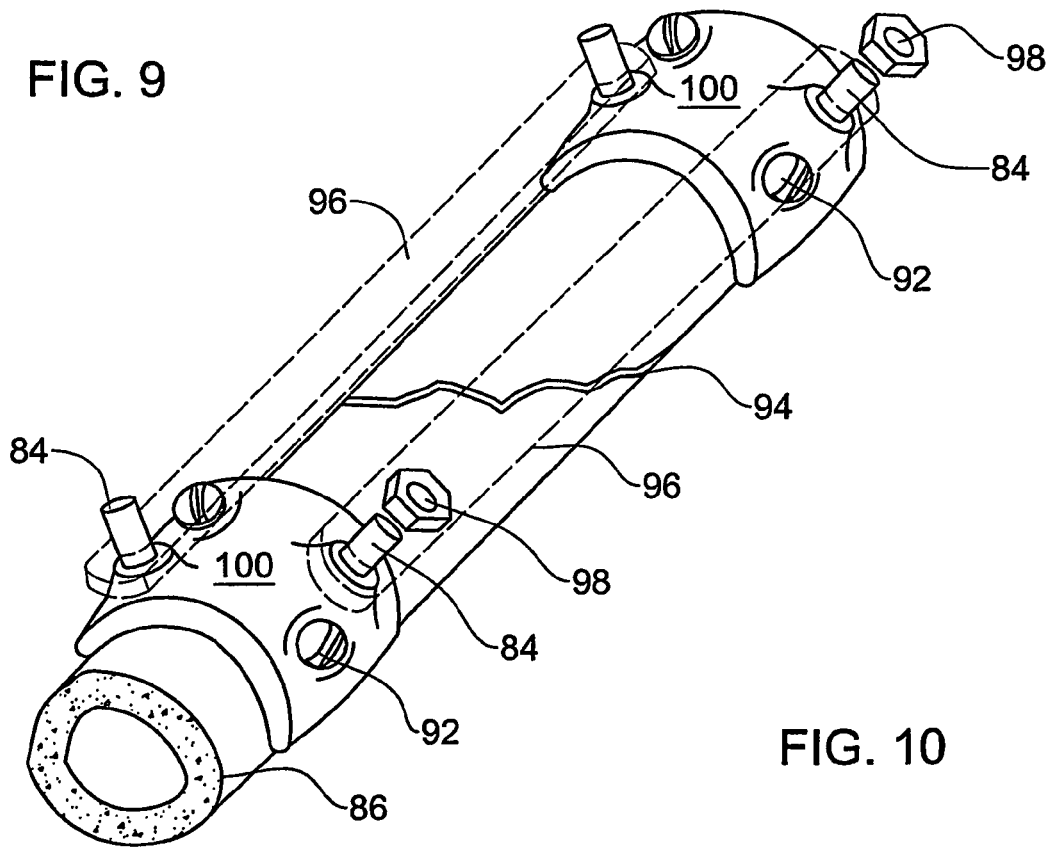
FIG. 10 is a perspective view of a fractured tubular bone fixed by means of two bars and two saddle clamps of the present invention.

FIG. 10 shows saddle clamps 100 with two threaded pins 84 each, connected by two plates 96 for more reliable fixing of the fractured bone 86.

The saddle clamps may be fixed by three or more screws. It will be appreciated that the arcuate or saddle surface of the clamp provides at least a third area of contact and support with the bone (when two screws are used) so that the clamp is in stable position. More screws may better distribute mechanical stress or load over the bone and between the screws. The saddle clamp, in appropriately changed configuration and size, may be used for fixing other bones.

According to the method of the present invention, an operation routine for fixing a fractured bone typically comprises the following steps. The patient is anesthetized, the limb where the fixing is to be performed is exposed, and the muscles detached from the bone to be treated, as in a normal limb operation. After preparation of the site on which the saddle clamps are to sit, the clamps are inserted into position on the bone, and self-tapping fixing screws are driven into the outer cortical wall of the bone. The fixing screws may pass through the opposite bone wall for better stability.

Then fixing plates or rods are attached to fix the broken parts of the bone together, and the patient's limb is surgically closed again. After healing of the bone, the saddle clamps and the fixing elements are surgically extracted.

Figure 5:
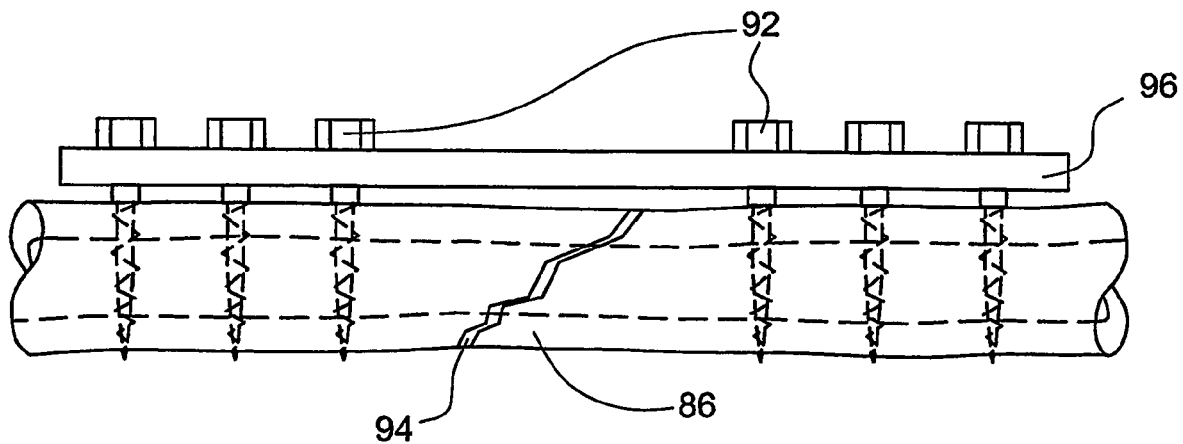
FIG. 5 is a schematic side view of a prior art tubular bone fixation using internal plate and screws.

It will be appreciated that the saddle clamp of the present invention needs less exposed length of the bone in comparison with the prior art screws and plate shown in FIG. 5.

Although a description of specific embodiments has been presented, it is contemplated that various changes could be made without deviating from the scope of the present invention. For example, the clamps of the present invention may be fixed to the tubular bone or vertebra by other fixing elements, such as nails or expanding anchors, etc.

The invention claimed is:

1. A saddle clamp for mounting on a vertebra and for carrying a bone-fixing member in a spinal fusion operation, the saddle clamp having a rigid body with a contact surface for contacting the vertebra and comprising a saddle surface and an arcuate surface, wherein:
   the saddle surface is defined between a first down-turned arch and an up-turned arch lying in transverse planes and having a common point;
   the arcuate surface is defined by a second down-turned arch and merges smoothly with the saddle surface; and
   top-most points of the arcuate surface are higher than the first down-turned arch.

2. The saddle clamp of claim 1, wherein the rigid body comprises at least two holes for passing therethrough fixing elements to be tightened to the vertebra, a first of the holes passing through the saddle surface, and a second of the holes passing through the arcuate surface.

3. The saddle clamp of claim 2, wherein axes of at least two of said holes converge towards said bone.

4. The saddle clamp of claim 2, wherein said first and second holes are positioned such that, when said saddle clamp is mounted to the vertebra, an axis of the first hole is directed into the pedicle and an axis of the second hole is directed into said edge and is convergent with the axis of the first hole.

5. The saddle clamp of claim 1, wherein said rigid body comprises at least one assembly element integral with the body for attaching thereto the bone-fixing member.

6. The saddle clamp of claim 5, wherein said assembly element is a threaded pin protruding from said rigid body.

7. The saddle clamp of claim 5, wherein said assembly element is a threaded nut built into said rigid body.

8. The saddle clamp of claim 1, wherein the rigid body comprises at least two holes for passing therethrough fixing elements to be tightened to the vertebra, a first of the holes passing through the saddle surface, and a second of the holes passing through the arcuate surface.

9. The saddle clamp of claim 8, being configured to have at least three points of contact with the vertebra when the saddle clamp is mounted thereon, at least two of the holes passing through the contact surface at least adjacent to two of the three points of contact so as to provide, upon tightening of the fixing elements, at least three spaced apart, non-collinear areas of contact and thereby firm attachment of the clamp to the vertebra.

10. A method for mounting a saddle clamp to a vertebra having a vertebra body and, at one side thereof, a pedicle, a superior facet with an edge, and a transverse process, said saddle clamp having a rigid body with a contact surface for contacting the vertebra and comprising a saddle surface and an arcuate surface, wherein the saddle surface is defined between a first down-turned arch and an up-turned arch lying in transverse planes and having a common point, and the arcuate surface is defined by a second down-turned arch and merges smoothly with the saddle surface, top-most points of the arcuate surface being higher than the first down-turned arch, said method including:

providing said saddle clamp with contact surface and passing holes suitably configured for said vertebra;

providing fixing elements;

exposing a suitable area of said vertebra;

drilling pilot holes in said vertebra corresponding to the passing holes, for anchoring said fixing elements, without penetrating further than the body of said pedicle, one pilot hole being drilled in said pedicle and a second pilot hole being drilled in said superior facet; and mounting said saddle clamp on said vertebra by inserting said fixing elements through the passing holes of said clamp and tightening them in the pilot holes of said vertebra, without said fixing elements penetrating said vertebra body.

11. The method of claim 10, wherein said fixing elements are screws.

12. The method of claim 10, wherein said second surface of the clamp is an arcuate surface adapted to receive said edge of the superior facet, and said second pilot hole is drilled into said edge.

13. The method of claim 10, further including adjusting the surface of said vertebra to said saddle clamp by cutting a portion of said edge of the superior facet.

14. The method of claim 10, wherein said fixing elements are screws, or nails, or expanding anchors.

15. The method of claim 10, wherein a second of said pilot holes is drilled with an axis convergent with the axis of a first pilot hole.

* * * * *